United States Patent [19]
Hoshino et al.

[11] Patent Number: 5,910,492
[45] Date of Patent: *Jun. 8, 1999

[54] OSTEOGENIC PROMOTING PHARMACEUTICAL COMPOSITION

[75] Inventors: Tetsuo Hoshino, Osaka; Hiroya Muranishi, Kyoto; Shigehisa Taketomi, Osaka; Susumu Iwasa, Kyoto, all of Japan

[73] Assignee: Takeda Chemical Industries, Ltd., Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/719,467

[22] Filed: Sep. 25, 1996

[30] Foreign Application Priority Data

Jun. 5, 1995 [JP] Japan ................................. 7-138036
Jan. 26, 1996 [JP] Japan ................................. 8-011686
Jun. 4, 1996 [WO] WIPO ........................ PCTJP9601506

[51] Int. Cl.⁶ ........................... A61K 31/67; A61K 31/66
[52] U.S. Cl. ........................... 514/114; 514/96; 514/119; 514/140
[58] Field of Search ........................... 514/96, 114, 119, 514/140

[56] References Cited

U.S. PATENT DOCUMENTS 5,071,841  12/1991  Sohda et al. ............................... 514/96
5,158,943  10/1992  Sohda et al. ............................... 514/96

FOREIGN PATENT DOCUMENTS 0 376 197   7/1990   European Pat. Off. .
0 460 488  12/1991   European Pat. Off. .
0 669 127   8/1995   European Pat. Off. .
0 719 782   7/1996   European Pat. Off. .
2 239 798   7/1991   United Kingdom .
93/00070    1/1993   WIPO .
96/01267    1/1996   WIPO .

OTHER PUBLICATIONS

Nelson et al., "Evaluation and Composition of Biodegradable Substances as Osteogenic Agents", Oral surgery, Oral Medicine, Oral Pathology, vol. 43, No. 6, (1977) pp. 836–843.

Miyamoto et al., "Polylactic Acid–Polyethylene Glycol Block Copolymer", Coin. Orth. and Rel. Research, vol. 294, (1993) pp. 33–343.

Healy et al., "Bioabsorbable Scaffolds for Bone Regneration", J. Dent. Res., vol. 72, (1993) p. 258.

*Primary Examiner*—Theodore J. Criares
*Attorney, Agent, or Firm*—Foley & Lardner

[57] ABSTRACT

This invention provides a pharmaceutical composition comprising a non-peptide osteogenic promoting substance and a biodegradable polymer, which can be safely used as a prophylactic/therapeutic agent for various bone diseases (e.g., bone fractures).

16 Claims, 2 Drawing Sheets

OSTEOGENIC PROMOTING PHARMACEUTICAL COMPOSITION

TECHNICAL FIELD

The present invention relates to a pharmaceutical composition having an enhanced osteogenic promoting activity comprising a non-peptide osteogenic promoting substance and a biodegradable polymer, which is a useful agent for treating and/or preventing bone diseases.

BACKGROUND ART

The bone diseases (e.g. bone fractures) can occur in all classes of people due to various causes of sports and traffic accidents. And, since it usually takes a long time to heal them, the bone diseases bring significantly hamperings to the patient's normal daily life. In recent years, the number of osteoporosis patients has increased with the aging of population. So, an incidence of limb bone fractures associated with osteoporosis has markedly increased in proportion to it. Femoral neck bone fracture, in particular, necessitates long-term hospitalization and often brings about internal complications including dementia caused by long-term hospitalization, and pose major social and economic problems. It is an urgent task to allow bone fracture patients to be early discharged from the hospital.

Bone fracture healing is a form of wound healing characterized by local occurrence and progression. Usually, various local factors function well at the site of fracture to promote the healing in vivo. Such factors include peptide-type bioactive substances such as bone morphogenetic proteins (BMPs) and transforming growth factors (TGFs), which have been reported to promote osteogenesis in animal models "Proceedings of the National Academy of Sciences, USA, vol. 87, pp. 2220–2224 (1990), and Endocrinology, vol. 124, pp. 2991–2993 (1989)".

With regard to non-peptide osteogenic promoting substance, for example, prostaglandin $A_1$ derivatives, vitamin $D_3$ derivatives, benzylphosphonic acid derivatives, phenolsulfophthalenic acid derivatives have been reported.

The above-mentioned peptide-type bioactive substances are peptides or proteins exceeding 5,000 in molecular weight, and are rapidly metabolized in vivo and lacking stability. With this in mind, some preparations have been produced in an attempt to obtain satisfactory stability, but all failed to achieve sufficient osteogenic promoting activity, and there are no preparations satisfactory as to quality etc. "Clinical Orthopaedics and Related Research, vol. 278, pp. 274–285". Also, the above-mentioned non-peptide osteogenic promoting substance are not clinically effective in terms of osteogenic promoting activity for bone fracture healing.

For these reasons, there is strong demand for a high-quality agent for treating bone disease that is highly stable, safe and active, and that is clinically effective in long-term treatment of bone fractures.

DISCLOSURE OF INVENTION

The present inventors made extensive investigation to resolve these problems, and found that an agent for treating bone disease comprising a non-peptide osteogenic promoting substance and a biodegradable polymer unexpectedly serves very well to promote bone fracture healing, with an enhanced osteogenic promoting activity of the non-peptide osteogenic promoting substance, than when administered alone. The present inventors made further investigation based on this finding, and developed the present invention.

Accordingly, the present invention relates to:
(1) a pharmaceutical composition comprising a non-peptide osteogenic promoting substance and a biodegradable polymer,
(2) a pharmaceutical composition according to (1), which further comprises a phosphoric acid or its salt,
(3) a pharmaceutical composition according to (1), wherein the non-peptide osteogenic promoting substance is non-steroid,
(4) a pharmaceutical composition according to (1), which is used for local administration,
(5) a pharmaceutical composition according to (1), which is used for promotion of bone fracture healing,
(6) a pharmaceutical composition according to (1), which is a sustained-release preparation,
(7) a pharmaceutical composition according to (1), wherein the non-peptide osteogenic promoting substance is a compound represented by the formula (I):

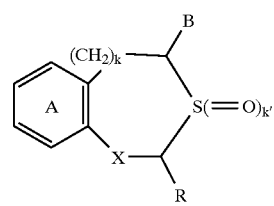

(I)

wherein ring A is an optionally substituted benzene ring; R is a hydrogen atom or an optionally substituted hydrocarbon group; B is an optionally esterified or amidated carboxyl group; X is —CH(OH)— or —CO—; k is 0 or 1; and k' is 0, 1 or 2, or its salt, (8) a pharmaceutical composition according to (7), wherein the ring A is a benzene ring which may be substituted by 1 or 2 substituents selected from the group consisting of a halogen, $C_{1-10}$ alkyl, $C_{1-10}$ alkoxy, —O—$(CH_2)_n$—O— wherein n is 1 to 3 and $C_{1-10}$ alkylthio, (9) a pharmaceutical composition according to (7), wherein B is —CON($R_1$)($R_2$) wherein $R_1$ and $R_2$ are independently a hydrogen atom, an optionally substituted hydrocarbon group or an optionally substituted 5 to 7 membered heterocyclic group,

(10) a pharmaceutical composition according to (9), wherein $R_1$ is hydrogen atom or a $C_{1-10}$ alkyl group, and $R_2$ is (i) a phenyl or phenyl-$C_{1-3}$ alkyl group which may be substituted by a halogen, $C_{1-6}$ alkoxy, mono- or di-$C_{1-6}$ alkoxyphosphoryl, mono- or di-$C_{1-6}$ alkoxyphosphoryl-$C_{1-3}$ alkyl,

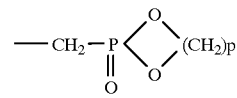

wherein p is an integer from 2 to 4 or $C_{1-6}$ alkoxycarbonyl or (ii) a 5- or 6-membered heterocyclic group containing 1 or 2 nitrogen atom(s) or 1 nitrogen atom and 1 sulfur atom, which may be substituted by a phenyl,

(11) a pharmaceutical composition according to (7), wherein R is a hydrogen atom, $C_{1-6}$ alkyl group or phenyl group,

(12) a pharmaceutical composition according to (7), wherein k is 1 and k' is 0,

(13) a pharmaceutical composition according to (1), wherein the non-peptide osteogenic promoting substance is an optically active compound represented by the formula:

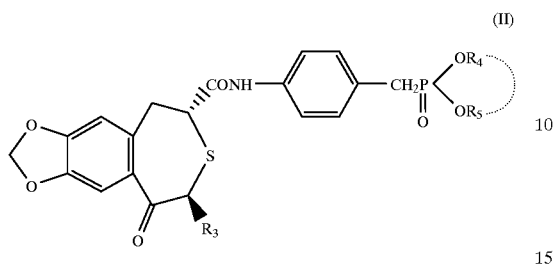

wherein $R_3$ is a lower alkyl group; and $R_4$ and $R_5$ are independently a lower alkyl group or bind together to form a lower alkylene group,

(14) a pharmaceutical composition according to (13), wherein $R_3$, $R_4$ and $R_5$ are independently a $C_{1-6}$ alkyl group,

(15) a pharmaceutical composition according to (1), wherein the compound is (2R, 4S)-(-)-N-[4-(diethoxyphosphorylmethyl)phenyl]-1,2,4,5-tetrahydro-4-methyl-7,8-methylenedioxy-5-oxo-3-benzothiepine-2-carboxamide,

(16) a pharmaceutical composition according to (1), wherein the ratio by weight of the biodegradable polymer based on the non-peptide osteogenic promoting substance is about 1 to 100 times,

(17) a pharmaceutical composition according to (1), which comprises (2R,4S)-(-)-N-[4-(diethoxyphosphorylmethyl)phenyl]-1,2,4,5-tetrahydro-4-methyl-7,8-methylenedioxy-5-oxo-3-benzothiepine-2-carboxamide, a biodegradable polymer,

(18) a pharmaceutical composition according to (17), which further comprises a phosphoric acid or its salt,

(19) a pharmaceutical composition according to (18), wherein the phosphoric acid or its salt is sodium phosphate,

(20) a pharmaceutical composition according to (17), wherein the content ratio of (2R,4S)-(-)-N-[4-diethoxyphosphorylmethyl)phenyl]-1,2,4,5-tetrahydro-4-methyl-7,8-methylenedioxy-5-oxo-3-benzothiepine-2-carboxamide based on the biodegradable polymer is about 5 to 30% (w/w), and the content ratio of sodium phosphate based on (2R, 4S)-(-)-[N-(diethoxyphosphorylmethyl)phenyl]-1,2,4,5-tetrahydro-4-methyl-7,8-methylenedioxy-5-oxo-3-benzothiepine-2-carboxamide and the biodegradable polymer is about 0.1 to 20% (w/w),

(21) a pharmaceutical composition according to (17), wherein the biodegradable polymer is a lactic acid-glycolic acid copolymer,

(22) a pharmaceutical composition according to (21), wherein the ratio of lactic aicd/glycolic acid is about 90/10 to 50/50 (w/w) and the weight-average molecular weight is about 8000 to 50000,

(23) a pharmaceutical composition according to (1), wherein the biodegradable polymer is an aliphatic polyester,

(24) a pharmaceutical composition according to (23), wherein the aliphatic polyester is a lactic acid-glycolic acid copolymer,

(25) a pharmaceutical composition according to (1), which is in the form of a suspension,

(26) a pharmaceutical composition according to (1), which is used for injection,

(27) use of a pharmaceutical composition according to (1) for manufacturing an agent for treating or preventing bone diseases,

(28) use of a biodegradable polymer to enhance osteogenic promoting activity,

(29) method for treating or preventing bone diseases in mammals which comprises administrating to a subject in need an effective amount of a pharmaceutical composition according to (1),

(30) method according to (29), wherein the bone diseases are bone fractures, and

(31) an agent for treating or preventing bone diseases with enhanced osteogenic promoting activity, which comprises a non-peptide osteogenic promoting substance and a biodegradable polymer, and so on.

Useful non-peptide osteogenic promoting substances of the present invention include the sulfur-containing heterocyclic compounds such as (2R,4S)-(-)-N-[4-(Diethoxyphosphorylmethyl)phenyl]-1,2,4,5-tetrahydro-4-methyl-7,8-methylenedioxy-5-oxo-3-benzothiepine-2-carboxamide or salts thereof described in U.S. Pat. No. 5,071,841, U.S. Pat. No. 5,158,943 and JP5294960, the benzopyrane derivatives such as N-(4-Dimethoxyphosphorylmethylphenyl)-4-oxo-4H-1-benzopyrane-2-carboxamide or salts thereof described in EP625522, the phosphonic acid derivatives such as Diethyl 4-(7-cyclohexyl-3,4-dihydro-2-naphthalenecarboxamide) benzylphosphonate or salts thereof described in WO96/01267, the prostaglandin $A_1$ derivatives described in Journal of Pharmacology and Experimental Therapeutics, vol. 258, pp. 1120–1126 (1991), the vitamin $D_3$ derivatives described in the Bioorganic & Medicinal Chemistry Letters, vol. 3, pp. 1815–1819 (1993), the benzylphosphonic acid derivatives described in EP524023, the bisphosphonic acids described in Bone, vol. 13, pp. 249–255 (1992), and the vitamin $K_2$ derivatives described in Biochemical and Biophysical Research Communications, vol. 187, pp. 814–820 (1992).

The pharmaceutical composition of the present invention may contain one or more non-peptide osteogenic promoting substances described above for active ingredient.

In the above-mentioned non-peptide osteogenic promoting substances, a compound represented by the following formula (I) or a salt thereof is preferably used for the present invention.

A compound of the formula (I):

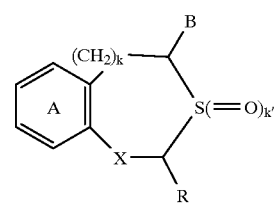

wherein ring A is an optionally substituted benzene ring; R is a hydrogen atom or an optionally substituted hydrocarbon group; B is an optionally esterified or amidated carboxyl group; X is —CH(OH)— or —CO—; k is 0 or 1; and k' is 0, 1 or 2, or its salt.

With respect to the formula (I), the substituent of the substituted benzene represented by ring A is exemplified by halogen atoms, nitro groups, optionally substituted alkyl groups, optionally substituted hydroxyl groups, optionally substituted thiol groups, optionally substituted amino groups, acyl groups, mono- or di-alkoxyphosphoryl groups, phosphono groups, optionally substituted aryl groups, optionally substituted aralkyl groups and optionally substituted aromatic heterocyclic groups. Of these substituents, 1 to 4, preferably 1 or 2, whether identical or not, may be present on the benzene ring.

The halogen atoms include fluorine, chlorine, bromine and iodine.

The alkyl groups of the optionally substituted alkyl groups include alkyl groups having 1 to 10 carbon atoms such as methyl, ethyl, propyl, isopropyl, butyl, isobutyl, sec-butyl, tert-butyl, pentyl, isopentyl, neopentyl, hexyl, heptyl, octyl, nonyl and decyl, and cycloalkyl groups having 3 to 7 carbon atoms such as cyclopropyl, cyclobutyl, cyclohexyl and cycloheptyl. These alkyl groups may be substituted by 1 to 3 substituents selected from halogen atoms (e.g., fluorine, chlorine, bromine, iodine), hydroxyl groups, alkoxy groups having 1 to 6 carbon atoms (e.g., methoxy, ethoxy, propoxy, butoxy, hexyloxy), mono- or di-$C_{1-6}$ alkoxyphosphoryl groups (e.g. methoxyphosphoryl, ethoxyphosphoryl, dimethoxyphosphoryl, diethoxyphosphoryl) and phosphono groups.

The substituted alkyl groups include trifluoromethyl, trifluoroethyl, trichloromethyl, hydroxymethyl, 2-hydroxyethyl, methoxyethyl, 1-methoxyethyl, 2-methoxyethyl, 2,2-diethoxyethyl, 2-diethoxyphosphorylethyl, phosphonomethyl and so on.

The substituted hydroxyl groups include alkoxy groups, alkenyloxy groups, aralkyloxy groups, acyloxy groups, aryloxy groups and so on. Preferable alkoxy groups are alkoxy groups having 1 to 10 carbon atoms (e.g., methoxy, ethoxy, propoxy, butoxy, tert-butoxy, pentyloxy, hexyloxy, heptyloxy, nonyloxy) and cycloalkoxy groups having 4 to 6 carbon atoms (e.g., cyclobutoxy, cyclopentoxy, cyclohexyloxy). Preferable alkenyloxy groups are alkenyloxy groups having 2 to 10 carbon atoms such as allyloxy, crotyloxy, 2-pentenyloxy, 3-hexenyloxy, 2-cyclopentenylmethoxy and 2-cyclohexenylmethoxy. Preferable aralkyloxy groups are aralkyloxy groups having 6 to 19 carbon atoms, with greater preference given to $C_{6-14}$ aryl-$C_{1-4}$ alkyloxy groups (e.g., benzyloxy, phenethyloxy). Preferable acyloxy groups are alkanoyloxy groups such as those having 2 to 10 carbon atoms (e.g., acetyloxy, propionyloxy, n-butyryloxy, hexanoyloxy). Preferable aryloxy groups are aryloxy groups having 6 to 14 carbon atoms (e.g., phenoxy, biphenyloxy). Further, these groups may be substituted by 1 to 3 substituents selected from the above-mentioned halogen atoms, hydroxyl groups, alkoxy groups having 1 to 6 carbon atoms, mono- or di-$C_{1-6}$ alkoxyphosphoryl groups, etc. The substituted hydroxyl groups include trifluoromethoxy, 2,2,2-trifluoroethoxy, difluoromethoxy, 2-methoxyethoxy, 4-chlorobenzyloxy and 2-(3,4-dimethoxyphenyl)ethoxy, and so on.

The substituted thiol groups include alkylthio groups, aralkylthio groups and acylthio groups. Preferable alkylthio groups are alkylthio groups having 1 to 10 carbon atoms (e.g., methylthio, ethylthio, propylthio, butylthio, pentylthio, hexylthio, heptylthio, nonylthio) and cycloalkylthio groups having 4 to 6 carbon atoms (e.g., cyclobutylthio, cyclopentylthio, cyclohexylthio). Preferable aralkylthio groups are aralkylthio groups having 7 to 19 carbon atoms, more preferably $C_{6-14}$ aryl-$C_{1-4}$ alkylthio groups such as benzylthio and phenethylthio. Preferable acylthio groups are alkanoylthio groups such as those having 2 to 10 carbon atoms (e.g., acetylthio, propionylthio, n-butyrylthio, hexanoylthio). Further, these substituted thiol groups may be substituted by 1 to 3 substituents selected from the above-mentioned halogen atoms, hydroxyl groups, alkoxy groups having 1 to 6 carbon atoms, mono- or di-$C_{1-6}$ alkoxyphosphoryl groups, etc. Specifically, the substituted thiol groups include trifluoromethylthio, 2,2,2-trifluoroethylthio, 2-methoxyethylthio, 4-chlorobenzylthio, 3,4-dichlorobenzylthio, 4-fluorobenzylthio, 2-(3,4-dimethoxyphenyl)ethylthio, and so on.

As substituents of the substituted amino groups, there may be used 1 or 2 identical or different substituents selected from the above-mentioned alkyl groups having 1 to 10 carbon atoms, alkenyl groups having 2 to 10 carbon atoms (e.g., allyl, vinyl, 2-penten-1-yl, 3-penten-1-yl, 2-hexen-1-yl, 3-hexen-1-yl, 2-cyclohexenyl, 2-cyclopentenyl, 2-methyl-2-propen-1-yl, 3-methyl-2-buten-1-yl), aryl groups having 6 to 14 carbon atoms (e.g. phenyl, naphthyl) and aralkyl groups having 7 to 19 carbon atoms (e.g. benzyl). These substituents may be substituted by the above-mentioned halogen atoms, alkoxy groups having 1 to 6 carbon atoms, mono- or di-$C_{1-6}$ alkoxyphosphoryl groups, phosphono groups, etc. Specifically, the substituted amino groups include methylamino, dimethylamino, ethylamino, diethylamino, dibutylamino, diallylamino, cyclohexylamino, phenylamino, N-methyl-N-phenylamino, N-methyl-N-(4-chlorobenzyl)amino and N,N-di(2-methoxyethyl)amino, and so on.

The acyl groups include organic carboxylic acid acyl groups and sulfonic acid acyl groups with a hydrocarbon group having 1 to 6 carbon atoms (e.g., methyl, ethyl, n-propyl, hexyl, phenyl). Useful organic carboxylic acyl groups are formyl, $C_{1-10}$ alkyl-carbonyl groups (e.g., acetyl, propionyl, butyryl, valeryl, pivaloyl, hexanoyl, octanoyl, cyclobutanecarbonyl, cyclohexanecarbonyl, cycloheptanecarbonyl), $C_{2-10}$ alkenyl-carbonyl groups (e.g., crotonyl, 2-cyclohexenecarbonyl), $C_{6-14}$ aryl-carbonyl groups (e.g., benzoyl), $C_{7-19}$ aralkyl-carbonyl groups (e.g., benzylcarbonyl, benzhydrylcarbonyl), 5- or 6-membered aromatic heterocyclic carbonyl groups (e.g, nicotinoyl, 4-thiazolylcarbonyl) and 5- or 6-membered aromatic heterocyclic acetyl groups (e.g., 3-pyridylacetyl, 4-thiazolylacetyl). Useful sulfonic acyl groups having 1 to 6 carbon atoms are methanesulfonyl and ethanesulfonyl. These acyl groups may be substituted by 1 to 3 substituents selected from the above-mentioned halogen atoms, hydroxyl groups, alkoxy groups having 1 to 6 carbon atoms, amino groups, etc. Specifically, the substituted acyl groups include trifluoroacetyl, trichloroacetyl, 4-methoxybutyryl, 3-cyclohexyloxypropionyl, 4-chlorobenzoyl and 3,4-dimethoxybenzoyl, and so on.

The mono- or di-alkoxyphosphoryl groups include mono-$C_{1-6}$ alkoxyphosphoryl groups such as methoxyphosphoryl, ethoxyphosphoryl, propoxyphosphoryl, isopropoxyphosphoryl, butoxyphosphoryl, pentyloxyphosphoryl and hexyloxyphosphoryl, and di-$C_{1-6}$ alkoxyphosphoryl groups such as dimethoxyphosphoryl, diethoxyphosphoryl, dipropoxyphosphoryl, diisopropoxyphosphoryl, dibutoxyphosphoryl, dipentyloxyphosphoryl and dihexyloxyphosphoryl, with preference given to di-$C_{1-6}$ alkoxyphosphoryl groups such as dimethoxyphosphoryl, diethoxyphosphoryl, dipropoxyphosphoryl, diisopropoxyphosphoryl, ethylenedioxyphosphoryl, dibutoxyphosphoryl, etc.

The aryl groups of the optionally substituted aryl groups include aryl groups having 6 to 14 carbon atoms such as phenyl, naphthyl and anthryl. These aryl groups may be substituted by 1 to 3 substituents selected from the above-mentioned alkyl groups having 1 to 10 carbon atoms, halogen atoms, hydroxyl groups, alkoxy groups having 1 to 6 carbon atoms, etc. Specifically, the substituted aryl groups include 4-chlorophenyl, 3,4-dimethoxyphenyl, 4-cyclohexylphenyl and 5,6,7,8-tetrahydro-2-naphthyl.

The aralkyl groups of the optionally substituted aralkyl groups include aralkyl groups having 7 to 19 carbon atoms such as benzyl, naphthylethyl and trityl. These aralkyl groups may be substituted by 1 to 3 substituents selected from the above-mentioned alkyl groups having 1 to 10 carbon atoms, halogen atoms, hydroxyl groups, alkoxy groups having 1 to 6 carbon atoms, etc. on the aromatic ring. Specifically, the substituted aralkyl groups include 4-chlorobenzyl, 3,4-dimethoxybenzyl, 4-cyclohexylbenzyl and 5,6,7,8-tetrahydro-2-naphthylethyl.

The aromatic heterocyclic groups of the optionally substituted aromatic heterocyclic groups include 5- to 6-membered aromatic heterocyclic groups having 1 to 4 atoms of nitrogen, oxygen and/or sulfur, such as furyl, thienyl, imidazolyl, thiazolyl, oxazolyl and thiadiazolyl. These aromatic heterocyclic groups may be substituted by 1 to 3 substituents selected from the above-mentioned alkyl groups having 1 to 10 carbon atoms, halogen atoms, hydroxyl groups, alkoxy groups having 1 to 6 carbon atoms, etc.

Provided that two alkyl groups are present as mutually adjoining substituents on the benzene ring A, they may bind together to form an alkylene group represented by the formula: —$(CH_2)_m$— wherein m is an integer from 3 to 5 (e.g., trimethylene, tetramethylene, pentamethylene). Provided that two alkoxy groups are present as mutually adjoining substituents on the benzene ring A, they may bind together to form an alkylenedioxy group represented by the formula: —O—$(CH_2)_n$—O— wherein n is an integer from 1 to 3 (e.g., methylenedioxy, ethylenedioxy, trimethylenedioxy). In these cases, a 5- to 7-membered ring is formed in cooperation with carbon atoms of the benzene ring.

With respect to the formula (I), R is a hydrogen atom or an optionally substituted hydrocarbon group.

The hydrocarbon group of the optionally substituted hydrocarbon group represented by R is exemplified by the above-mentioned alkyl groups (preferably alkyl groups having 1 to 10 carbon atoms), alkenyl groups (preferably alkenyl groups having 2 to 10 carbon atoms), aryl groups (preferably aryl groups having 6 to 14 carbon atoms) and aralkyl groups (preferably aralkyl groups having 7 to 19 carbon atoms). Useful substituents on the hydrocarbon group include the above-mentioned 5- or 6-membered aromatic heterocyclic groups, halogen atoms, di-$C_{1-6}$ alkoxyphosphoryl groups and phosphono groups.

Preferable examples of R are an unsubstituted alkyl groups having 1 to 6 carbon atoms such as methyl, ethyl, propyl, isopropyl, butyl, isobutyl, sec-butyl, tert-butyl, pentyl, neopentyl and hexyl.

With respect to the formula (I), B is an optionally esterified or amidated carboxyl group.

The esterified carboxyl group represented by B is exemplified by alkoxycarbonyl group, preferably $C_{1-10}$ alkoxycarbonyl groups (e.g., methoxycarbonyl, ethoxycarbonyl, propoxycarbonyl, butoxycarbonyl), aryloxy-carbonyl groups, preferably $C_{6-14}$ aryloxy-carbonyl groups (e.g., phenoxycarbonyl), and aralkyloxycarbonyl groups, preferably $C_{7-19}$ aralkyloxy-carbonyl groups (e.g., benzyloxycarbonyl).

The amidated carboxyl group represented by B is exemplified by an optionally substituted carbamoyl group represented by the formula: —$CON(R_1)(R_2)$ wherein $R_1$ and $R_2$ independently are a hydrogen atom, an optionally substituted hydrocarbon group or an optionally substituted 5- to 7-membered heterocyclic group.

The hydrocarbon group of the optionally substituted hydrocarbon group represented by $R_1$ or $R_2$ is exemplified by the above-mentioned alkyl groups, preferably alkyl groups having 1 to 10 carbon atoms (e.g., methyl, ethyl, propyl, isopropyl, butyl, isobutyl, sec-butyl, tert-butyl, pentyl, isopentyl, neopentyl, hexyl, heptyl, octyl, nonyl, decyl), alkenyl groups, preferably those having 2 to 10 carbon atoms (e.g., allyl, vinyl, 2-penten-1-yl, 3-penten-1-yl, 2-hexen-1-yl, 3-hexen-1-yl, 2-cyclohexenyl, 2-cyclopentenyl, 2-methyl-2-propen-1-yl, 3-methyl-2-buten-1-yl), aryl groups, preferably those having 6 to 14 carbon atoms (e.g., phenyl, naphthyl, anthryl), and aralkyl groups, preferably those having 7 to 19 carbon atoms (e.g., benzyl, naphthyl, trityl). These hydrocarbon groups may be substituted by 1 to 3 substituents selected from halogen atoms (e.g., fluorine, chlorine, bromine, iodine), hydroxyl groups, alkoxy groups having 1 to 6 carbon atoms (e.g., methoxy, ethoxy, propoxy, butoxy, tert-butoxy, pentyloxy, hexyloxy), amino groups which may be substituted by alkyl groups having 1 to 6 carbon atoms (e.g., amino, methylamino, ethylamino, dimethylamino, diethylamino, dipropylamino), amino groups substituted by $C_{1-10}$ acyl groups (e.g., acetylamino, propionylamino, benzoylamino), carbamoyl groups which may be substituted by alkyl groups having 1 to 6 carbon atoms (e.g., carbamoyl, methylcarbamoyl, dimethylcarbamoyl, diethylcarbamoyl), $C_{1-6}$ alkoxy-carbonyl groups (e.g., methoxycarbonyl, ethoxycarbonyl, propoxycarbonyl), mono- or di-alkoxyphosphoryl groups (e.g. mono- or di-$C_{1-6}$ alkoxyphosphoryl groups such as dimethoxyphosphoryl, diethoxyphosphoryl, ethylenedioxyphosphoryl), mono- or di-alkoxyphosphorylalkyl groups (e.g. mono- or di-$C_{1-6}$ alkoxyphosphoryl-$C_{1-3}$ alkyl groups such as methoxyphosphorylmethyl, ethoxyphosphorylmethyl, methoxyphosphorylethyl, ethoxyphosphorylethyl, dimethoxyphosphorylmethyl, diethoxyphosphorylmethyl, dimethoxyphosphoryethyl, diethoxyphosphoryethyl), a moiety:

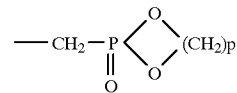

wherein p is an integer from 2 to 4, phosphono groups, the above-mentioned aromatic heterocyclic groups, etc.

The 5- to 7-membered heterocyclic group of the optionally substituted 5- to 7-membered heterocyclic group represented by $R_1$ or $R_2$ is exemplified by 5- to 7-membered heterocyclic groups containing a sulfur, nitrogen or oxygen atom, 5- or 6-membered heterocyclic groups containing 2 to 4 nitrogen atoms, and 5- or 6-membered heterocyclic groups containing 1 or 2 nitrogen atom(s) and a sulfur or oxygen atom. These heterocyclic groups may be condensed with a 6-membered ring containing 2 or fewer nitrogen atoms, a benzene ring or a 5-membered ring containing a sulfur atom.

As substituents of the substituted 5- to 7-membered heterocyclic group represented by $R_1$ and $R_2$, there may be used 1 to 4 of the same substituents as those for the substituted hydrocarbon group represented by $R_1$ and $R_2$ above.

Preferable examples of the 5- to 7-membered heterocyclic group represented by $R_1$ and $R_2$ include 2-pyridyl, pyrimidyl, pyrazinyl, pyridazinyl, pyrazolyl, imidazolyl, thiazolyl, oxazolyl, pyrido[2,3-d]pyrimidyl, benzopyranyl, 1,8-naphthyridyl, quinolyl, thieno[2,3-b]pyridyl, tetrazolyl, thiadiazolyl, oxadiazolyl, triazinyl, triazolyl, thienyl, pyrrolyl, pyrrolinyl, furyl, pyrrolidinyl, benzothienyl, indolyl, imidazolidinyl, piperidyl, piperidino, piperazinyl, morpholinyl and morpholino.

The moiety: —$NR_1(R_2)$ may form a 5- to 7-membered ring by binding together with $R_1$ and $R_2$. Such rings include morpholine, piperidine, thiomorpholine, homopiperidine, piperidine, pyrrolidine, thiazolidine and azepine.

The substituted alkyl groups as preferable examples of the optionally substituted hydrocarbon group represented by $R_1$ and $R_2$ include trifluoromethyl, trifluoroethyl, difluoromethyl, trichloromethyl, 2-hydroxyethyl, 2-methoxyethyl, 2-ethoxyethyl, 2,2-dimethoxyethyl, 2,2-diethoxyethyl, 2-pyridylmethyl, 3-pyridylmethyl, 4-pyridylmethyl, 2-(2-thienyl)ethyl, 3-(3-furyl)propyl, 2-morpholinoethyl, 3-pyrrolylbutyl, 2-piperidinoethyl, 2-(N,N-dimethylamino)ethyl, 2-(N-methyl-N-ethylamino) ethyl, 2-(N,N-diisopropylamino)ethyl, 5-(N,N-dimethylamino)pentyl, N,N-dimethylcarbamoylethyl, N,N-dimethylcarbamoylpentyl, ethoxycarbonylmethyl, isopropoxycarbonylethyl, tert-butoxycarbonylpropyl, 2-diethoxyphosphorylethyl, 3-dipropoxyphosphorylpropyl, 4-dibutoxyphosphorylbutyl, ethylenedioxyphosphorylmethyl, 2-phosphonoethyl and 3-phosphonopropyl. The preferable substituted aralkyl groups include 4-chlorobenzyl, 3-(2-fluorophenyl)propyl, 3-methoxybenzyl, 3,4-dimethoxyphenethyl, 4-ethylbenzyl, 4-(3-trifluoromethylphenyl)butyl, 4-acetylaminobenzyl, 4-dimethylaminophenethyl, 4-diethoxyphosphorylbenzyl and 2-(4-dipropoxyphosphorylmethylphenyl)ethyl. The preferable substituted aryl groups include 4-chlorophenyl, 4-cyclohexylphenyl, 5,6,7,8-tetrahydro-2-naphthyl, 3-trifluoromethylphenyl, 4-hydroxyphenyl, 3,4,5-trimethoxyphenyl, 6-methoxy-2-naphthyl, 4-(4-chlorobenzyloxy)phenyl, 3,4-methylenedioxyphenyl, 4-(2,2,2-trifluoroethoxy)phenyl, 4-propionylphenyl, 4-cyclohexanecarbonylphenyl, 4-dimethylaminophenyl, 4-benzoylaminophenyl, 4-diethoxycarbamoylphenyl, 4-tert-butoxycarbonylphenyl, 4-diethoxyphosphorylphenyl, 4-diethoxyphosphorylmethylphenyl, 4-(2-diethoxyphosphorylethyl)phenyl, 2-diethoxyphosphorylmethylphenyl, 3-diethoxyphosphorylmethylphenyl, 4-dipropoxyphosphorylphenyl, 4-(2-phosphonoethyl)phenyl, 4-phosphonomethylphenyl and 4-phosphonophenyl. The preferable substituted 5- to 7-membered heterocyclic groups include 5-chloro-2-pyridyl, 3-methoxy-2-pyridyl, 5-methyl-2-benzothiazolyl, 5-methyl-4-phenyl-2-thiazolyl, 3-phenyl-5-isoxazolyl, 4-(4-chlorophenyl)-5-methyl-2-oxazolyl, 3-phenyl-1,2,4-thiadiazol-5-yl, 5-methyl-1,3,4-thiadiazol-2-yl, 5-acetylamino-2-pyrimidyl, 3-methyl-2-thienyl, 4,5-dimethyl-2-furanyl and 4-methyl-2-morpholinyl.

With respect to the formula (I), ring A is preferably a benzene ring which may be substituted by 1 or more, more preferably 1 or 2 substituents selected from ① halogen atoms, ② optionally substituted alkyl groups, ③ optionally substituted hydroxyl groups, ④ optionally substituted thiol groups and/or ⑤ optionally substituted amino groups.

More preferably, ring A is a benzene ring which may be substituted by 1 or 2 substituents selected from the above-mentioned halogen atoms, alkyl groups having 1 to 10 carbon atoms (furthermore preferably 1 to 5 carbon atoms), alkoxy groups having 1 to 10 carbon atoms (furthermore preferably 1 to 5 carbon atoms), alkylenedioxy groups represented by the formula: —O—$(CH_2)_n$—O— wherein n is an integer from 1 to 3, and/or alkylthio groups having 1 to 10 carbon atoms (furthermore preferably 1 to 5 carbon atoms).

Most preferably, ring A is a benzene ring which may be substituted by an alkylenedioxy group represented by the formula: —O—$(CH_2)_n$—O— wherein n is an integer from 1 to 3.

B is preferably an alkoxy-carbonyl-group or a group represented by the formula: —$CON(R_1)(R_2)$ wherein $R_1$ and $R_2$ independently are a hydrogen atom, an optionally substituted hydrocarbon group or an optionally substituted 5- to 7-membered heterocyclic group.

With respect to $R_1$ and $R_2$ above, $R_1$ is preferably a hydrogen atom or an alkyl group having 1 to 10 carbon atoms (e.g. methyl, ethyl, propyl), and $R_2$ is preferably a phenyl or phenyl-$C_{1-3}$ alkyl group which may be substituted by a halogen atom (e.g. fluorine, chlorine, bromine), a $C_{1-6}$ alkoxy (e.g. methoxy, ethoxy), a mono- or di-alkoxyphosphoryl (preferably a mono- or di-$C_{1-6}$ alkoxyphosphoryl such as diethoxyphosphoryl), a mono- or di-alkoxyphosphorylalkyl (preferably a mono- or di-$C_{1-6}$ alkoxyphosphoryl-$C_{1-3}$ alkyl such as diethoxyphosphorylmethyl) or a $C_{1-6}$ alkoxycarbonyl (e.g. methoxycarbonyl, ethoxycarbonyl), or a 5- or 6-membered heterocyclic group (e.g. pyridyl) which may be substituted by a phenyl and that contains 1 or 2 nitrogen atom(s) or a nitrogen atom and a sulfur atom.

More preferable example of $R_1$ and $R_2$ is "$R_1$ is a hydrogen atom, and $R_2$ is a phenyl group substituted by a mono- or di-$C_{1-6}$ alkoxyphosphoryl-$C_{1-3}$ alkyl (e.g. 4-diethoxyphosphorylmethylphenyl)".

With respect to the formula (I), X is —CH(OH)— or —CO—, preferably —CO—.

With respect to the formula (I), k is 0 or 1, and k' is 0, 1 or 2, preferably k is 1, and k' is 0.

R is preferably a hydrogen atom, an alkyl group having 1 to 6 carbon atoms (e.g. methyl, ethyl) or a phenyl group.

The compound (I) is preferably an optically active compound represented by the formula (II):

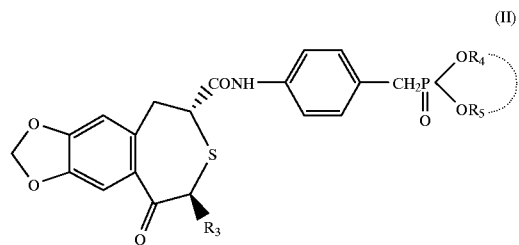

(II)

wherein $R_3$ is a lower alkyl group; $R_4$ and $R_5$ independently are a lower alkyl group or bind together to form a lower alkylene group.

The lower alkyl group represented by $R_3$, $R_4$ or $R_5$ in the formula (II) is exemplified by alkyl groups having 1 to 6 (preferably 1 to 4) carbon atoms such as methyl, ethyl, propyl, isopropyl, butyl, isobutyl, sec-butyl, tert-butyl, pentyl, isopentyl, neopentyl and hexyl. $R_4$ and $R_5$ may bind together to form a lower alkylene group. In this case, a moiety:

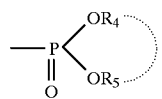

may represent a moiety:

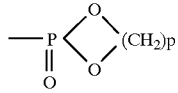

wherein p is an integer from 2 to 4.

Preferable groups for $R_3$, $R_4$ and $R_5$ include alkyl groups having 1 to 4 carbon atoms such as methyl and ethyl.

The compound (II) is an optically active compound of the (2R,4S) configuration, and contains substantially no compound of the (2S,4R) configuration. The compound (II) of which optical purity is nearly 100% is preferable.

Most preferably, the compound (II) is, for example, (2R,4S)-(−)-N-[4-(diethoxyphosphorylmethyl)phenyl]-1,2,4,5-tetrahydro-4-methyl-7,8-methylenedioxy-5-oxo-3-benzothiepine-2-carboxamide (hereinafter also referred to as compound A).

The salt of a non-peptide osteogenic promoting substance of the present invention is preferably a pharmaceutically acceptable salt. Pharmaceutically acceptable salts include salts with inorganic bases, salts with organic bases and salts with basic or acidic amino acids. Inorganic bases capable for forming such salts include alkali metals (e.g., sodium, potassium) and alkaline earth metals (e.g., calcium, magnesium), such organic bases include trimethylamine, triethylamine, pyridine, picoline, N,N-dibenzylethylenediamine and diethanolamine, such inorganic acids include hydrochloric acid, hydrobromic acid, hydroiodic acid, phosphoric acid, nitric acid and sulfuric acid, such organic acids include formic acid, acetic acid, trifluoroacetic acid, oxalic acid, tartaric acid, fumaric acid, maleic acid, methanesulfonic acid, benzenesulfonic acid, p-toluenesulfonic acid and citric acid, and such basic or acidic amino acids include arginine, lysine, aspartic acid and glutamic acid.

The non-peptide osteogenic promoting substance for the present invention can be produced by, for example, the commonly known method (e.g. U.S. Pat. No. 5,071,841, U.S. Pat. No. 5,158,943 described above and the method described below or a modification thereof. For example, the compound (I) or a salt thereof can be produced by subjecting a compound represented by the formula (III):

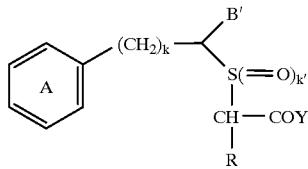

wherein B' is an esterified carboxyl group; Y is a hydroxy group or a halogen atom; the other symbols are of the same definitions as described above, or a salt thereof to a cyclizing reaction, if necessary, then carrying out an oxidizing reaction and/or a hydrolyzing reaction, or a hydrolyzing reaction and a subsequent amidating reaction, or a hydrolyzing reaction and a subsequent amidating reaction, and then subjecting the reaction product to an oxidizing reaction, followed by a reducing reaction as necessary.

For example, the compound (II) is produced by reacting an optically active compound represented by the formula (IV):

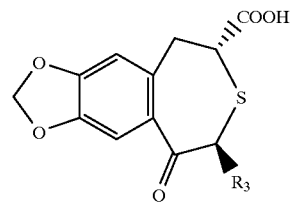

wherein $R_3$ is of the same definition as described above, or a reactive derivative at the carboxyl group thereof or a salt thereof, with a compound represented by the formula (V):

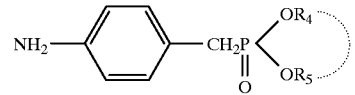

wherein $R_4$ and $R_5$ are of the same definitions as described above, a reactive derivative at the amino group thereof or a salt thereof.

Preferable reactive derivatives of the amino group on the compound (V) include Schiff's base type imino or enamine form tautomeric isomers resulting from reaction of the compound (V) and a carbonyl compound such as an aldehyde (e.g., acetaldehyde) or a ketone (e.g., acetone); silyl derivatives resulting from reaction of the compound (V) and a silyl compound such as bis(trimethylsilyl)acetamide, mono(trimethylsilyl)acetamide or bis(trimethylsilyl)urea; and derivatives resulting from reaction of the compound (V) and phosphorus trichloride or phosgene.

Preferable reactive derivatives of the carboxyl group on the compound (IV) include acid halides, acid anhydrides, activated amides and activated esters which are obtained by conventional method. The preferable reactive derivatives include acid chlorides; acid azides; mixed acid anhydrides with a substituted phosphoric acid such as dialkylphosphoric acid, phenylphosphoric acid, diphenylphosphoric acid, dibenzylphosphoric acid or halogenated phosphoric acid, a dialkylphosphorous acid, a sulfurous acid, a thiosulfuric acid, a sulfuric acid, a sulfonic acid such as methanesulfonic acid, an aliphatic carboxylic acid such as acetic acid, propionic acid, butyric acid, isobutyric acid, pivalic acid, pentanoic acid, isopentanoic acid or trichloroacetic acid, or an aromatic carboxylic acid such as benzoic acid; symmetric acid anhydrides; activated amides with imidazole, 4-substituted imidazole, dimethylpyrazole, triazole or tetrazole; activated esters such as cyanomethyl ester, methoxymethyl ester, dimethyliminomethyl ester, vinyl ester, propargyl ester, p-nitrophenyl ester, trichlorophenyl ester, pentachlorophenyl ester, mesylphenyl ester, phenylazophenyl ester, phenylthio ester, p-nitrophenyl ester, p-cresylthio ester, carboxymethylthio ester, pyranyl ester, pyridyl ester, piperidyl ester or 8-quinolylthio ester; and esters with N-hydroxy compounds such as N,N-dimethylhydroxylamine, 1-hydroxy-2-(1H)-pyridone, N-hydroxysuccinimide, N-hydroxyphthalimide, 1-hydroxy-1H-benzotriazole and N-hydroxy-5-norbornene-2,3-dicarboxyimide. These reactive derivatives can be optionally chosen according to the kind of the compound (IV).

Preferable salts of reactive derivatives of the compound (IV) or (V) include base salts exemplified by alkali metal salts such as sodium salt and potassium salt, alkaline earth metal salts such as calcium salt and magnesium salt, ammonium salt, and organic base salts such as trimethylamine salt, triethylamine salt, pyridine salt, picoline salt, dicyclohexylamine salt and N,N-dibenzylethylenediamine salt.

This reaction is normally carried out in an ordinary solvent such as water, alcohol (e.g. methanol, ethanol), acetone, dioxane, acetonitrile, chloroform, methylene chloride, ethylene chloride, tetrahydrofuran, ethyl acetate, N,N-dimethylformamide or pyridine, but can be carried out in any other organic solvent, as long as it does not interfere with the reaction. These ordinary solvents may be used in mixture with water. In this reaction, when the compound (IV) or (V) is used in the form of free acid or salt thereof, this reaction is preferably carried out in the presence of an ordinary condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide; N,N'-carbonylbis(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride; diphenylphosphorylazide; thionyl chloride; oxalyl chloride; lower alkyl haloformate such as ethyl chloroformate or isopropyl chloroformate; triphenylphosphine; 2-ethyl-7-hydroxybenzisoxazolium salt; 2-ethyl-5-(m-sulfophenyl)isoxazolium hydroxide intramolecular salt; N-hydroxybenzotriazole; 1-(p-chlorobenzenesulfonyloxy)-6-chloro-1H-benzotriazole; or Wilsmeier's reagent as prepared by reacting N,N'-dimethylformamide with thionyl chloride, phosgene, trichloromethyl chloroformate or phosphorus oxychloride. Also desirable is the method using a condensing agent such as N,N'-dicyclohexylcarbodiimide in the presence of N-hydroxybenzotriazole or N-hydroxy-5-norbornene-endo-2,3-dicarboxyimide. This reaction may also be carried out in the presence of an inorganic or organic base such as alkali metal hydrogen carbonate tri(lower)-alkylamine, pyridine, N-(lower)-alkylmorpholine or N,N-di (lower)alkylbenzylamine. Although reaction temperature is not subject to limitation, this reaction is normally carried out under cooling to heating conditions (−10 to 120° C.). Reaction time is normally about 0.5 to 100 hours, preferably about 1 to 50 hours.

The compound (II) thus obtained may be isolated and purified by known means of separation and purification such as concentration, concentration under reduced pressure, solvent extraction, crystallization, recrystallization, redissolution and chromatography.

The starting compound (IV) can, for example, be produced by optically resolving the racemate of the compound (IV) disclosed in U.S. Pat. No. 5,158,943. Specifically, the optically active compound is produced by preparing a salt of the racemate of the compound (IV) and an optically active base (e.g., optically active α-methylbenzylamine, brucine, quinine, cinchonine), repeating fractional crystallization based on the solubility difference between the resulting diastereomers to obtain a sparingly soluble salt in pure form, then performing acid treatment. The other optically active compound can be produced by esterifying the racemate of the compound (IV) with an optically active alcohol (e.g., optically active methyl lactate, methyl mandelate), preparing the other ester in pure form on the basis of the physical property difference between the resulting diastereomers, then performing hydrolysis.

The biodegradable polymer of the present invention is a polymer that is soluble or insoluble in water and degradable in vivo. Examples of such polymers include fatty acid polyesters such as polymers, copolymers and their mixture of one or more kinds of α-hydroxycarboxylic acids (e.g., lactic acid, glycolic acid, 2-hydroxybutyric acid, 2-hydroxyvaleric acid, 2-hydroxy-3-methylbutyric acid, 2-hydroxycaproic acid, 2-hydroxyisocaproic acid, 2-hydroxycaprylic acid), hydroxydicarboxylic acids (e.g., malic acid) and hydroxytricarboxylic acids (e.g., malic acid), lactic acid caprolactones, valerolactones, etc., and derivatives thereof (e.g., block polymers of polylactic acid, polyglycolic acid and polyethylene glycol), poly-α-cyanoacrylates, poly-β-hydroxybutyric acid, polyalkylene oxalates (e.g., polytrimethylene oxalate, polytetramethylene oxalate), polyortho-esters, polyortho-carbonates, polycarbonates (e.g., polyethylene carbonate, polyethylenepropylene carbonate), polyamino acids (e.g., poly-γ-benzyl-L-glutamic acid, poly-L-alanine, poly-γ-methyl-L-glutamic acid), hyarulonates, polystyrene, polymethacrylic acid, acrylic acid-methacrylic acid copolymers, polyamino acids, dakin stearate, ethyl cellulose, acetyl cellulose, nitrocellulose, maleic anhydride copolymers, ethylene-vinyl acetate copolymers, polyvinyl acetate, polyacrylamide, collagen, gelatin, fibrin and hydroxyapatite.

These biodegradable polymers may be in the form of homopolymers or copolymers of two or more kinds, or these mixtures.

Polymerization may be of the random, block or graft type.

Preferable biodegradable polymers include aliphatic polyesters.

From the viewpoint of biodegradability and biocompatibility, polymers and copolymers synthesized from one or more kinds of α-hydroxycarboxylic acids-are preferred. Specifically, copolymers synthesized from one or more kinds of lactic acid, glycolic acid, 2-hydroxybutyric acid, 2-hydroxyvaleric acid etc., or mixtures thereof are used.

The biodegradable copolymer for the present invention can be produced by commonly known methods such as that described in EP172636, or a modification thereof.

Although the above-mentioned α-hydroxycarboxylic acids may be of the D-, L- or D,L-configuration, the D,L-configuration is preferred.

Homopolymers of the above-mentioned α-hydroxycarboxylic acids include homopolymers of lactic acid, glycolic acid and 2-hydroxybutyric acid. The preferable α-hydroxycarboxylic acid is lactic acid. Copolymers of the above-mentioned α-hydroxycarboxylic acids include copolymers of glycolic acid and the other α-hydroxycarboxylic acids. Preferable α-hydroxycarboxylic acids are lactic acid and 2-hydroxybutyric acid. Specifically, useful copolymers include lactic acid-glycolic acid copolymers and 2-hydroxybutyric acid-glycolic acid copolymers, with preference given to lactic acid-glycolic acid copolymers, etc.

The average molecular weight of these biodegradable polymers for the present invention is preferably chosen from the range of about 2,000 to 800,000, more preferably about 5,000 to 200,000.

The weight-average molecular weight of a lactic acid homopolymer (hereinafter also referred to as polylactic acid) is preferably about 5,000 to 100,000, more preferably about 6,000 to 50,000. A polylactic acid can, for example, be synthesized by commonly known production methods such as that described in EP172636.

The content ratio of lactic acid and glycolic acid in a lactic acid-glycolic acid copolymer is preferably about 100/0 to 50/50 (w/w), and more preferably about 90/10 to 50/50

(w/w). The weight-average molecular weight of the lactic acid-glycolic acid copolymer is preferably about 5,000 to 100,000, more preferably about 8,000 to 50,000. The lactic acid-glycolic acid copolymer can be synthesized by a commonly known production method such as that described in EP172636. The copolymer is preferably synthesized by catalyst-free dehydration polymerization condensation.

With respect to the 2-hydroxybutyric acid-glycolic acid copolymer, the content ratio is preferably such that glycolic acid accounts for about 40 to 70 mol %, and 2-hydroxybutyric acid accounts for the remaining portion. The weight-average molecular weight of the 2-hydroxybutyric acid-glycolic acid copolymer is preferably about 5,000 to 100,000, more preferably about 8,000 to 50,000. The 2-hydroxybutyric acid-glycolic acid copolymer can be synthesized by a commonly known production method such as that described in EP172636. The copolymer is preferably synthesized by catalyst-free dehydration polymerization condensation.

The above-described 2-hydroxybutyric acid-glycolic acid copolymer may be used in mixture with polylactic acid. When the 2-hydroxybutyric acid-glycolic acid copolymer is used in mixture with polylactic acid, the mixing ratio of 2-hydroxybutyric acid/glycolic acid is about 10/90 to 90/10 (% by weight), preferably about 25/75 to 75/25 (% by weight).

In the present specification, weight-average molecular weight is defined as that based on polystyrene measured by gel permeation chromatography (GPC). Measurements were taken using a GPC column KF804L×2 (produced by Showa Denko) and an RI monitor L-3300 (produced by Hitachi Ltd.) with chloroform as a mobile phase.

The amount of biodegradable polymer is variable according to the strength of the pharmacological activity of the non-peptide osteogenic promoting substance, the speed and duration of drug release from the biodegradable polymer and so on, as long as the desired purpose is accomplished. For example, the biodegradable polymer is used in amounts about 0.2 to 10,000 times (ratio by weight), preferably about 1 to 1,000 times, more preferably about 1 to 100 times, for the amount of the bioactive substance.

The pharmaceutical composition of the present invention can be produced by ordinary methods of producing a pharmaceutical composition, for example, it can be produced by dispersing a non-peptide osteogenic promoting substance in a biodegradable polymer, or by filling a non-peptide osteogenic promoting substance in a previously shaped hollow biodegradable polymer. Specifically, useful methods include the in-water drying method, the phase separation method, the spray drying method, and modifications thereof.

The shape of pharmaceutical composition of the present invention as obtained by a production method mentioned above may be in the form of, for example, fine particles, spheres, rods, needles, pellets, films or creams, but the shape is not limited thereto as long as the desired purpose is accomplished.

In the present specification, a pharmaceutical composition of fine particles is also referred to as a microcapsule or a microsphere.

Example methods of producing microcapsules are described below.

(1) In-Water Drying Method (o/w Method)

In this method, an organic solvent solution comprising a biodegradable polymer is first prepared. The organic solvent used to produce the pharmaceutical composition of the present invention preferably has a boiling point of not higher than 120° C. Such organic solvents include halogenated hydrocarbons (e.g., dichloromethane, chloroform, chloroethane, dichloroethane, trichloroethane, carbon tetrachloride), aliphatic esters (e.g., ethyl ester, butyl ester), ethers (e.g., ethyl ether, isopropyl ether) and aromatic hydrocarbons (e.g., benzene, toluene, xylene). These solvents may be used in combination of two or more kinds in appropriate ratios. The organic solvent is preferably dichloromethane or acetonitrile, more preferably dichloromethane. The concentration of biodegradable polymer in the organic solvent solution is normally chosen over the range of about 0.01 to 80% (w/w), preferably about 0.1 to 70% (w/w), and more preferably about 1 to 60% (w/w), although varying depending on molecular weight of biodegradable polymer and organic solvent type, etc.

The non-peptide osteogenic promoting substance is added and dissolved into the organic solvent solution comprising the biodegradable polymer thus obtained, if necessary after lyophilized or vacuum dried. The amount of non-peptide osteogenic promoting substance is about 0.001 to 90% (w/w), preferably about 0.01 to 80% (w/w), and more preferably about 0.1 to 50% (w/w), based on the concentration of biodegradable polymer in the organic solvent solution, although varying depending on drug type, mechanism of action on osteogenesis, effect duration, etc.

The organic solvent solution thus prepared is then added to an aqueous phase to form an o/w emulsion using a turbine type mechanical stirrer or the like. The volume of the aqueous phase is normally chosen from the range of about 1 to 10,000 times, preferably about 2 to 5,000 times, and more preferably about 5 to 2,000 times, for the volume of the oil phase.

An emulsifier may be added to the aqueous phase. The emulsifier may be any one as long as it is capable of forming a stable o/w emulsion. Examples of such emulsifiers include anionic surfactants, nonionic surfactants, polyoxyethylene castor oil derivatives, polyvinylpyrrolidone, polyvinyl alcohol, carboxymethyl cellulose, lecithin, gelatin and hyaluronic acid. These may be used in combination as appropriate. The concentration of emulsifier in the aqueous phase is preferably about 0.001 to 20% (w/w), more preferably about 0.01 to 10% (w/w), and further more preferably about 0.05 to 5% (w/w).

Solvent evaporation from the oil phase can be achieved by commonly used methods, including the method in which the solvent is evaporated under normal or gradually reduced pressure during stirring using a propeller stirrer or magnetic stirrer, etc., and the method in which the solvent is evaporated while the degree of vacuum is adjusted using a rotary evaporator, etc. The obtained microcapsules are separated by centrifugal method or filtration, after which they are washed with, for example, water or heptane, several times to remove free non-peptide osteogenic-promoting substances, emulsifier, etc. adhering to the microcapsule surface. The microcapsules are then again dispersed in distilled water, etc. and lyophilized.

In the above-described o/w method, microcapsules may be produced by the s/o/w method, in which a non-peptide osteogenic promoting substance is dispersed in an organic solvent solution comprising a biodegradable polymer.

(2) In-Water Drying Method (w/o/w Method)

In this method, a non-peptide osteogenic promoting substance or a salt thereof is first dissolved or dispersed in water to obtain a concentration specified above to yield an internal aqueous phase, if necessary with dissolving or suspending by adding a drug-retaining substance such as a protein (e.g., gelatin), seaweed (e.g., agar), polysaccharide (e.g., alginic acid), synthetic high-molecular substance (e.g., polyvinyl alcohol), basic amino acid (e.g., arginine, lysine) or the like. The internal aqueous phase may be supplemented with an organic acid such as acetic acid, oxalic acid or citric acid, an inorganic acid such as carbonic acid or phosphoric acid, an alkali metal hydroxide such as sodium hydroxide, a basic amino acid such as arginine or lysine or a salt thereof (e.g., salts with organic acids such as acetic acid, oxalic acid, citric acid or salts with inorganic acids such as carbonic acid, phosphoric acid and hydrochloric acid) as a pH regulator for keeping the stability and solubility of the non-peptide osteogenic promoting substance or salt thereof. As a stabilizer for the non-peptide osteogenic promoting substance, there may be added a protein (e.g., albumin, gelatin), starch derivative (e.g. dextrin, pullulan etc.), organic acid (e.g., citric acid), ethylenediaminetetraacetic acid alkali metal salt (e.g., sodium ethylenediaminetetraacetate), sulfurous acid hydrogen alkali metal salt (e.g., sodium hydrogen sulfite), synthetic high-molecular substance (e.g., polyethylene glycol) or the like. Commonly preservatives may also be added p-oxybenzoates (e.g., methyl paraben, propyl paraben), benzyl alcohol, chlorobutanol and thimerosal. The additional amount of non-peptide osteogenic promoting substance is about 0.001 to 90% (w/w), preferably about 0.01 to 80% (w/w), and more preferably about 0.1 to 50% (w/w), although varying depending on drug type, mechanism of action on osteogenesis or effect duration, etc.

The obtained internal aqueous phase is added to a solution (oil phase) containing the biodegradable polymer, followed by emulsifying treatment, to yield a w/o emulsion. This emulsification is achieved by a known dispersing methods which include the intermittent shaking method, the method using a mixer such as a propeller shaker or a turbine shaker, the colloidal mill method, the homogenizer method and the ultrasonication method. The above-described solution (oil phase) containing the biodegradable polymer is a solution prepared by dissolving the biodegradable polymer in an organic solvent. This solvent may be any solvent as long as its boiling point is not higher than about 120° C. and it is immiscible with water. Such solvents include halogenated hydrocarbons (e.g., dichloromethane, chloroform, chloroethane, dichloroethane, trichloroethane, carbon tetrachloride), aliphatic esters (e.g., ethyl acetate, butyl acetate), ethers (e.g., ethyl ether, isopropyl ether) and aromatic hydrocarbons (e.g., benzene, toluene, xylene). These solvents may be used in combination of two or more kinds in appropriate ratios.

The produced w/o emulsion is then added to an aqueous phase to yield a w/o/w emulsion, from which the oil phase solvent is evaporated off, to yield microcapsules. The specific procedure for this production is the same as that described in (1) above.

(3) Phase Separation Method

In this method, a coacervating agent is gradually added to the above-described w/o emulsion under the stirring to precipitate and solidify the biodegradable polymer. The coacervating agent can be used silicon oil, vegetable oils and fats (e.g., sesame oil, soybean oil, corn oil, cotton seed oil, coconut oil, linseed oil), mineral oils, hydrocarbons (e.g., n-hexane, n-heptane) as long as it is a polymeric, mineral oil or vegetable oil compound which can be mixed with the solvent of the biodegradable polymer and which does not dissolve the polymer for encapsulation. These may be used in combination of two or more kinds.

The obtained microcapsules are, after filtration and separation of them, repeatedly washed with heptane, etc. to remove the coacervating agent. The free drug and solvent are then removed by using the same manner as in-water drying method. To prevent particle flocculation during washing, antiflocculants: water-soluble sugars such as mannitol, lactol, glucose and starches (e.g., corn starch), amino acids such as glycine and alanine, and proteins such as gelatin, fibrin and collagen may be added.

(4) Spray Drying Method

For producing microcapsules by this method, the above-described w/o emulsion is sprayed via a nozzle into the drying chamber of a spray drier to volatilize the organic solvent and water in the fine droplets in a very short time, and microcapsules are obtained. The nozzle is exemplified by the double-fluid nozzle, pressure nozzle and rotary disc nozzle. To prevent microcapsule flocculation, an aqueous solution of the above-described antiflocculant may be sprayed via another nozzle, while the w/o emulsion is sprayed. The microcapsules thus obtained may be warmed under reduced pressure to facilitate the removal of the water and solvent contained them.

In addition to the above-described microcapsules, the pharmaceutical composition of the present invention can be produced by dissolving a biodegradable polymer dispersed a non-peptide osteogenic promoting substance and forming the solution into spheres, rods, needles, pellets, films or the like, by an appropriate method. The biodegradable polymer dispersed non-peptide osteogenic promoting substance is produced in accordance with, for example, the method described in U.S. Pat. No. 3,773,919.

In addition, the pharmaceutical composition of the present invention can also be produced by pulverizing to appropriate particle size a biodegradable polymer dispersed the non-peptide osteogenic promoting substance by a method such as that described in JP62234656, which employs a turbo counter jet mill pulverizer or an ultrasonic jet pulverizer. Specifically, the non-peptide osteogenic promoting substance is added to an organic solvent containing the biodegradable polymer, and dissolved therein. The solid solution obtained by vacuum drying is then coarsely pulverized and sieved, followed by solvent removal, after which the coarse particles are pulverized to controlled particle size using an ultrasonic jet pulverizer to yield the pharmaceutical of the present invention.

The pharmaceutical composition of the present invention may be used in the form of microcapsules as such, or formulated into various dosage forms with microcapsules, spheres, rods, needles, pellets, films or creams as starting material. The pharmaceutical composition of the present invention may contain a phosphoric acid or its salt (e.g. sodium phosphate, potassium phosphate) at the rate of 0 to 30%. The pharmaceutical composition of the present invention can also be administered as a non-oral agent for local administration (e.g., injectable preparations of intramuscular, subcutaneous, organs or joints, etc., of solid preparations such as, indwellable preparations, granules and powders, liquid preparations such as suspensions, and ointments).

The injectable preparation can be prepared as aqueous suspension by suspending microcapsules in water, along with a dispersing agent (e.g., surfactants such as Tween 80 and HCO-60, polysaccharides such as carboxymethyl cellulose, sodium alginate and hyarulonic acid, and polysorbate), a preservative (e.g., methyl paraben, propyl paraben), an isotonizing agent (e.g., sodium chloride, mannitol, sorbitol, glucose), buffer (e.g. calcium carbonate), pH adjusting agent (e.g. sodium phosphate, potassium phosphate), etc., and may be also prepared as an oily suspension by dispersing microcapsules in a vegetable oil such as sesame oil or corn oil with or without a phospholipid such as lecithin, or a moderate-length fatty acid triglyceride (e.g., MIGLYOL 812).

The phosphate can enhance the osteogenic promoting activity of the pharmaceutical composition of the present invention.

The concentration of sodium phosphate or potassium phosphate in the injectable preparation is about 0.1 mM to 500 mM, preferably about 1 mM to 100 mM.

The preferable formation of the present invention is as follows.

(A) a lactic acid-glycolic acid copolymer:
wherein the ratio of lactic acid/glycolic acid is about 90/10 to 50/50 (w/w) and the weight-average molecular weight is about 8000 to 50000, (B) (2R,4S)-(-)-N-[4-(diethoxyphosphorylmethyl) phenyl]-1,2,4,5-tetrahydro-4-methyl-7,8-methylenedioxy-5-oxo-3-benzothiepine-2-carboxamide, and (c) sodium phosphate.

The content ratio of (B) based on (A) is about 5 to 30% (w/w).

The content ratio of (C) based on (A) and (B) is about 0.1 to 20% (w/w).

When microcapsules are used as an injectable suspension, for instance, their particle size is chosen over the range from about 0.1 to 300 µm of average particle diameter, as long as the requirements concerning the degree of dispersion and needle passage are met. Preferably, the particle size is about 1 to 150 µm, more preferably about 2 to 100 µm.

The pharmaceutical composition of the present invention is preferably a suspension as described above.

The pharmaceutical composition of the present invention is preferably in the form of fine particles. This is because said pharmaceutical composition is less likely to cause excess pain to the patient when administered through an injection needle for ordinary subcutaneous or intramuscular injection.

The pharmaceutical composition of the present invention is preferably an injectable preparation.

Methods of preparing microcapsules as a sterile preparation include, but are not limited to, the method in which the entire production process is sterile, the method in which gamma rays are used as sterilant, and the method in which an antiseptic is added.

The pharmaceutical composition of the present invention can be used to prevent and treat bone diseases (e.g., bone fractures, refracture, osteoporosis, osteomalacia, Behcet's syndrome of bone, ankylosing spondylitis, rheumatoid arthritis, and joint tissue destruction caused by deformation gonarthritis and the related diseases), to repair bone tissue after surgery for multiple myeloma, lung cancer, breast cancer, etc., and to regenerate periodontal tissue in periodontopathy, because it shows a sustained release property with the enhanced activity of the non-peptide osteogenic promoting substance, and has a sustained-release time for 1 week to 3 months, depending on biodegradable polymer type and content, etc. The pharmaceutical composition of the present invention is particularly effective in bone fracture patients, because the patients are usually fixed the affected portion and covered with plaster bandage and desire to promote the healing by a single administration rather than by multiple administrations. The sustained-release preparation consisting of the pharmaceutical composition of the present invention can be used in combination of the other active agents. For example, in the case of the compound represented by the formula (I) as osteogenic promoting substance, as the active agent to be combined with, mention is made of a formulation of calcium compound (e.g. sodium carbonate), calcitonin, vitamin D (e.g. alfacalcidol), sex hormone (e.g. estrogen, estradiol), prostaglandin $A_1$, bisphosphonic acid, ipriflavone, fluoride compound (e.g. sodium fluoride), vitamin $K_2$, BMP (bone morphogenetic protein), FGF (fibroblast growth factor), PDGF (platelet derived growth factor), TGF-β (transforming growth factor-β), IGF-1 (insulin like growth factor-1), IGF-2 (insulin like growth factor-2), PTH (parathyroid hormone), and so on.

With low toxicity, the pharmaceutical composition of the present invention can be safely used in mammals (e.g., humans, bovines, horses, pigs, dogs, cats, mice, rats, rabbits).

The pharmaceutical composition of the present invention is expected to serve as a safe preparation of high efficacy proving a constant drug effect with low toxicity and meeting the requirements of the prevention and treatment of bone diseases, repair of damaged bone tissue, and regeneration of periodontal tissue in periodontitis etc., because it releases the drug constantly over an extend period of time. For example, when the pharmaceutical composition of the present invention is used to treat bone fractures (e.g., femoral neck fracture), it can be allowed to efficiently exhibit its osteogenic promoting action in local and to significantly shorten the healing time, which is conventionally 2 to 6 months following onset of bone fracture. Accordingly, patients shortly return to normal social life, and can be also prevented various complication caused by senile bone fractures.

The dose of the pharmaceutical composition of the present invention may be an effective amount of the non-peptide osteogenic promoting substance, although depending on type and content of the non-peptide osteogenic promoting substance, release time of the drug, and subject animals, etc. For example, when the pharmaceutical composition of the present invention is used in the form of microcapsules to treat a bone fracture portion, it may be administered at about 0.01 to 500 mg, preferably about 5 to 50 mg, based on the active ingredient content (e.g., compound (I)), per adult (weighing 50 kg) per dosing, once every week to every 3 months.

BEST MODE FOR CARRYING OUT THE INVENTION

Figure 1:
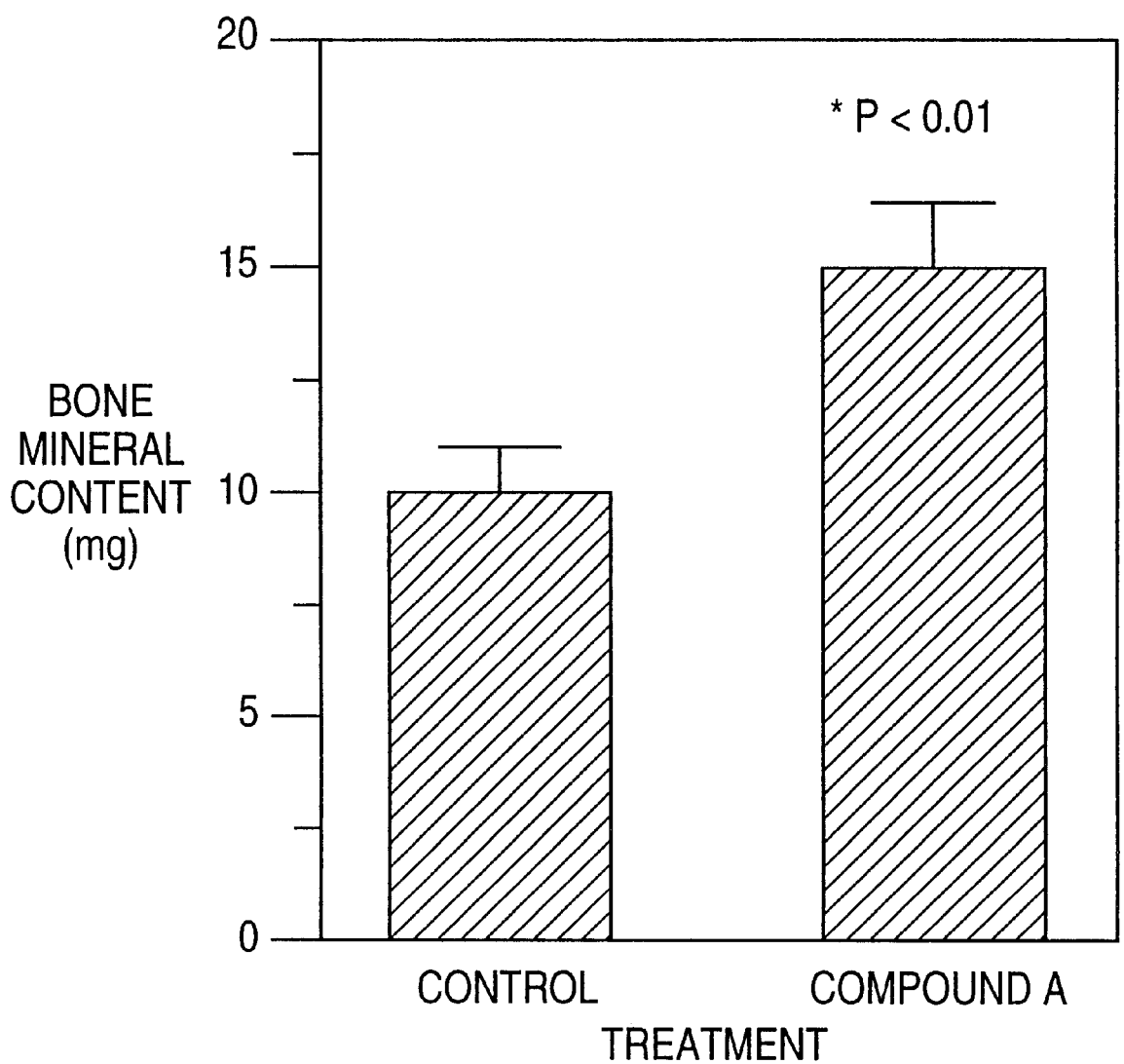
FIG. 1 is a graphic representation of fibular bone mineral content (mg) at 2 weeks after administration of microcapsule containing compound A and placebo microcapsule (control) to rats.

The present invention is hereinafter described in more detail by means of the following reference examples, working examples and test examples, which examples are not to be construed as limitative. In the working examples and test examples below, room temperature is defined as a temperature between about 0 and 30° C.

EXAMPLES

Reference Example 1
Production of (2R,4S)-(−)-1,2,4,5-tetrahydro-4-methyl-7,8-methylenedioxy-5-oxo-3-benzothiepine-2-carboxylic acid (R)-α-methoxycarbonylbenzyl ester A solution of 1-ethyl-3-(3-dimethylaminopropyl) carbodiimide hydrochloride (12.59 g) in dichloromethane (200 ml) was added drop by drop to a solution of (±)-t-1,2,4,5-tetrahydro-4-methyl-7,8-methylenedioxy-5-oxo-3-benzothiepine-2-carboxylic acid (15.34 g) and methyl (R)-(−)-mandelic acid (18.19 g) in N,N-dimethylformamide (DMF) (200 ml) at 0° C., followed by the addition of 4-dimethylaminopyridine (DMAP) (3.34 g). After being stirred at 0° C. for 1 hour and at room temperature for 15 hours, the mixture was poured over water and extracted with ethyl acetate. The ethyl acetate layer was washed with water and dried ($MgSO_4$), after which the solvent was distilled off. The residual crystal was collected by filtration, washed with ether-hexane, and twice recrystallized from ethyl acetate-hexane to yield the title compound (4.09 g, yield 17%).

Melting point: 140–141° C. Optical rotation $[\alpha]_D$ (23° C.): −244.2° (c=0.50, $CHCl_3$)

Reference Example 2
Production of (2R,4S)-(−)-1,2,4,5-tetrahydro-4-methyl-7,8-methylenedioxy-5-oxo-3-benzothiepine-2-carboxylic acid A mixture of (2R,4S)-(−)-1,2,4,5-tetrahydro-4-methyl-7,8-methylenedioxy-5-oxo-3-benzothiepine-2-carboxylic acid (R)-α-methoxycarbonylbenzyl ester as obtained in Reference Example 1 (4.18 g), acetic acid (45 ml) and concentrate hydrochloric acid (30 ml) was stirred for 30 minutes under refluxing conditions. The reaction mixture was poured over water (800 ml). The resulting crystal was collected by filtration, and dissolved in ethyl acetate (150 ml). The ethyl acetate layer was washed with water and dried ($MgSO_4$), after which the solvent was distilled off. The residual crystal was collected by filtration, washed with hexane, and recrystallized from ethyl acetate-hexane to yield the title compound (1.62 g, yield 59%) in the form of a colorless needle.

Melting point: 194–195° C. Optical rotation $[\alpha]_D$ (23° C.): −210.8° (c=0.50, $CH_3OH$)

Reference Example 3
Production of (2R,4S)-(−)-N-[4-(diethoxyphosphorylmethyl)phenyl]-1,2,4,5-tetrahydro-4-methyl-7,8-methylenedioxy-5-oxo-3-benzothiepine-2-carboxamide (compound A)

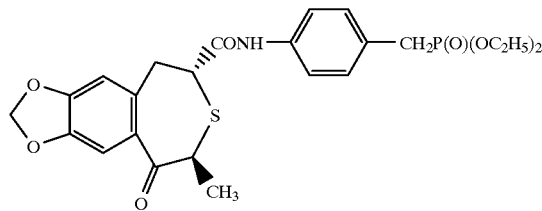

A solution of 1-ethyl-3-(3-dimethylaminopropyl) carbodiimide hydrochloride (0.39 g) in dichloromethane (7 ml) was added drop by drop to a solution of (2R,4S)-(−)-1,2,4,5-tetrahydro-4-methyl-7,8-methylenedioxy-5-oxo-3-benzothiepine-2-carboxylic acid (0.47 g) as obtained in Reference Example 2 (0.41 g) and diethyl 4-aminobenzylphosphonate (0.41 g) in N,N-dimethylformamide (DMF) (7 ml) at 0° C., followed by the addition of 1-hydroxybenzotriazole (HOBt) (0.28 g). After being stirred at 0° C. for 1 hour and at room temperature (25° C.) for 15 hours, the mixture was poured over water and extracted with ethyl acetate. The ethyl acetate layer was washed with water and dried ($MgSO_4$), after which the solvent was distilled off. The residual crystal was collected by filtration, and recrystallized from ethyl-hexane acetate and methanol-hexane to yield compound A (0.37 g, 44%) in the form of a colorless prism.

Melting point: 181–182° C. Optical rotation $[\alpha]_D$ (23° C.): −187.4° (c=0.50, $CHCl_3$)

Example 1

A dichloromethane solution of a lactic acid-glycolic acid copolymer "hereinafter also referred to as PLGA; lactic acid-glycolic acid content ratio (mol %) and weight-average molecular weight based on GPC measurement are shown in Table 1; produced by Wako Pure Chemical Industry" and a lactic acid homopolymer (hereinafter also referred to as PLA) was prepared (hereinafter also referred to as solution A), using a formula shown in Table 1. Similarly, a dichloromethane solution of compound A was also prepared using a formula shown in Table 1 (hereinafter also referred to as solution B). Solutions A and B were uniformly mixed together. The mixture was injected to 0.1% aqueous solution of polyvinyl alcohol (EG-40, produced by The Nippon Synthetic Chemical Industry) (hereinafter also referred to as PVA solution) set at 15° C. in advance in a volume specified in Table 1, and emulsified using a turbine-type homomixer at 7,000 rpm to yield an o/w emulsion, which was then stirred at room temperature for 3 hours to volatilize the dichloromethane. After solidification, the oil phase was centrifuged at 2,000 rpm using a centrifuge (05PR-22, Hitachi Ltd.). The collected microcapsule fraction was again dispersed in distilled water, then centrifuged, followed by washing of released drug, etc. The collected microcapsules were again dispersed in a small amount of distilled water, then lyophilized. Microcapsules of the particle sizes shown in Table 1 were obtained. The ratio of microcapsules incorporated in compound A was 100%.

TABLE 1

| | | Solution A | | | | Solution B | | PVA Liquid | Particle |
|---|---|---|---|---|---|---|---|---|---|
| Micro-capsules | Polymer | L/G Content Ratio* (mol %) | Weight-average Molecular Weight | Polymer Weight (g) | Dichloro-methane (ml) | Compound A Weight (g) | Dichloromethane (ml) | Volume (ml) | Size (μm) |
| No. 1 | PLGA | 75/25 | 10500 | 2.4 | 2.5 | 0.1 | 1.0 | 400 | 24 |
| No. 2 | PLGA | 75/25 | 6500 | 2.4 | 1.0 | 0.1 | 1.0 | 400 | 50 |
| No. 3 | PLGA | 75/25 | 17100 | 2.4 | 1.5 | 0.1 | 1.0 | 400 | 38 |
| No. 4 | PLA | 100/0 | 12000 | 2.4 | 2.0 | 0.1 | 1.0 | 800 | 37 |
| No. 5 | PLGA | 90/10 | 20000 | 2.4 | 2.0 | 0.1 | 1.0 | 400 | 65 |
| No. 6 | PLGA | 85/15 | 12100 | 2.4 | 2.0 | 0.1 | 1.0 | 800 | 51 |

*Lactic acid/Glycolic acid Content Ratio

Example 2

About 8 g of a lactic acid-valerolactone copolymer (PLV 2500ML, produced by Taki Chemical, hereinafter also referred to as PLV) or a glycolic acid-caprolactone copolymer (PGC 2500MG, produced by Taki Chemical, hereinafter also referred to as PGC) was placed in a centrifugal tube and heated to about 50° C. in a water bath. About 80 mg of compound A was mixed in each tube, followed by uniform dispersion, to yield an ointment preparation, which was stored at a cold place.

Example 3

500 mg of microcapsule No. 1 as obtained in Example 1 was uniformly dispersed in two test tubes of fibrinogen solution for Tisseel (produced by Nippon Zoki Pharmaceutical). Two test tubes of thrombin solution for Tisseel were gradually added. Subsequently, each mixture was immediately aspirated into a plastic syringe. The syringe was kept standing at 37° C. for 30 minutes to solidify the content. After solidification, the content was extruded from the syringe tip and cut using a razor into pellets about 200 μl in volume.

Example 4

Four milligrams of compound A was filled in the bone defect filler hollow hydroxyapatite (Boneceram P, produced by Sumitomo Pharmaceuticals, 3 mm diameter, 14 mm length, 1 mm pore size). Both ends of the hollow were sealed with clay.

Example 5

To microcapsule No. 3 as obtained in Example 1 which contains compound A (content ratio 4%), 20% pulverized gelatin (produced by Nitta Gelatin) was added, to yield a microcapsule-containing tablet preparation 5.5 mm in diameter and 125 mg in weight.

Example 6

Microcapsule No. 7 containing compound A (content ratio 10%) was prepared in the same manner as in Example 1, except that PLGA having a lactic acid-glycolic acid content ratio of 85/15 (mol %) and weight-average molecular weight of 14,900 (produced by Wako Pure Chemical Industry). Mean particle size was 31 μm.

Example 7

A dichloromethane solution containing 2.4 g of PLGA (produced by Wako Pure Chemical Industry) whose the lactic acid/glycolic acid content ratio is 85/15 and the weight-average molecular weight is 14,900 and 0.1 g of the compound A was prepared in the same manner as Example 1. And 0.2 g of estradiol was added into the solution. Further PVA solution was put into the solution to obtain O/W emulsion. Microcapsule No. 8 containing the compound A and estradiol was prepared. The mean particle size was 27 μm.

Test Example 1

500 mg of microcapsule No. 1 as obtained in Example 1 was weighed accurately and transferred to a glass centrifugal tube and kept standing at 37° C. in a powder state. After a given time, the microcapsules were dissolved in a small amount of acetonitrile and quantitatively analyzed by high performance liquid chromatography (hereinafter also referred to as HPLC). The stability tests are shown in Table 2.

The drug content was over 95% even after 4 weeks.

TABLE 2

| Days | Remaining (%) |
|---|---|
| 0 | 99 |
| 7 | 97 |
| 14 | 97 |
| 21 | 95 |
| 28 | 96 |

Test Example 2

Microcapsule Nos. 2, 3 and 4 as obtained in Example 1, each 5 mg, were weighed accurately and transferred to a glass vial, followed by shaking in a 37° C. water bath (TAITEC, incubator M-100, 115 strokes/minute) in the presence of 10 ml of a release test solution (phosphate buffer supplemented with 10% bovine serum albumin, pH 7.0). To each 100 μl sample taken over time, 100 μl of acetonitrile was added. After shaking, this mixture was centrifuged. The resulting supernatant was assayed by HPLC to determine the amount of compound A released. The release tests are shown in Table 3.

Three kinds of microcapsules of different release patterns were obtained.

TABLE 3

| Days | Remaining (%) | | |
|---|---|---|---|
| | No. 2 | No. 3 | No. 4 |
| 0.0 | 0.0 | 0.0 | 0.0 |
| 0.3 | 81.7 | 8.4 | 5.7 |
| 1.0 | 92.2 | 18.1 | 10.5 |
| 2.0 | 91.0 | 27.3 | 14.8 |
| 3.0 | 88.6 | 36.6 | — |
| 7.0 | 86.4 | 67.6 | 33.3 |
| 9.0 | 82.9 | 70.8 | — |
| 11.0 | 82.8 | 74.1 | — |

Test Example 3

Microcapsule Nos. 3 to 6 as obtained in Example 1, each 25 mg, were dispersed in 0.3 ml of a dispersant (solution of 1.5 mg of carboxymethyl cellulose, 0.3 mg of polysorbate 20 and 15 mg of mannitol in distilled water) and subcutaneously injected to the heads of male SD rats (n=5) at 5 weeks of age under ether anesthesia using a 22G injection needle. Rats were killed at given time intervals after administration. Microcapsules remaining at the administration site were taken out and assayed by HPLC to determine the amount of compound A in the microcapsules. The results are shown in Table 4.

Various kinds of microcapsules of different release patterns were obtained in vivo as well. Specifically, microcapsule No. 3 was found to have a sustained-release duration of 1 month, microcapsule Nos. 4 and 5 are over 1 month, and microcapsule No. 6 is 3 weeks.

TABLE 4

| Days | Remaining (%) | | | |
|---|---|---|---|---|
| | No. 3 | No. 4 | No. 5 | No. 6 |
| 0 | 100 | 100 | 100 | 100 |
| 1 | 89 | 82 | 62 | 76 |
| 7 | 47 | 70 | 62 | 47 |
| 14 | 20 | 48 | 55 | 23 |
| 21 | 17 | 33 | 44 | 2 |
| 28 | 2 | 17 | 32 | 6 |

Test Example 4

An ointment preparation as obtained in Example 2 was filled in an ointment tube. A chip for micropipet attachment was attached to the tube end to facilitate administration to animals. The ointment was subcutaneously administered to the backs of male SD rats (n=5) at 5 weeks of age under ether anesthesia. The amount of administration was based on the tube weight difference between before and after administration. Rats were killed at given time intervals. The amount of residual compound A was determined by HPLC. The results are shown in Table 5.

An ointment preparation releasing the entire dose in 1 to 2 weeks was obtained.

TABLE 5

| Days | Remaining (%) | |
|---|---|---|
| | PGC | PLV |
| 0 | 100 | 100 |
| 1 | 36 | 10 |
| 7 | 9 | 0 |
| 14 | 1 | 1 |

Test Example 5

Under pentobarbital anesthesia, the heads of male SD rats (n=8) at 6 weeks of age were incised, and the periosteum was detached. A hole 4 mm in diameter was then made in the left calvaria using a dental drill. After 1 week following suturing, 25 mg of microcapsule No. 3 as obtained in Example 1 was dispersed in 0.3 ml of a dispersant (solution of 1.5 mg of carboxymethyl cellulose, 0.3 mg of polysorbate 20 and 15 mg of mannitol in distilled water) and subcutaneously administered to the right temple using a 22G injection needle. For control, rats receiving 0.3 ml of the above dispersant alone were used. Three weeks later, the rats were killed. The calvaria was excised and subjected to soft X-ray analysis. Using the photograph obtained, the area of newly formed bone at the bone defect portion was determined by image analysis.

A significant increase in the area of newly formed bone was noted in the microcapsule administration group, demonstrating the excellent osteogenic promoting activity of the pharmaceutical composition of the present invention.

Test Example 6

Under pentobarbital anesthesia, the left legs of male SD rats (n=8) at 6 weeks of age were incised, and the central portion of the left fibula was exposed then cut using a cutter. 25 mg of microcapsule No. 1 as obtained in Example 1 was embedded in the fibula cutting portion, followed by suturing. Two weeks later, the rats were killed. The fibula was excised and analyzed using a bone mineral analyzer (DSC-600, Aloca Co., Ltd., Tokyo) to determine the bone mineral content. The bone mineral content in the untreated right fibula was also determined. The measurement for the right fibula was subtracted from that for the left fibula to obtain the bone mineral content in the callus. For control, compound A-free placebo microcapsules were prepared in the same manner as that used to prepare microcapsule No. 1, and compared with the counterpart in the same manner as in Test Example 5. The results are shown in FIG. 1.

Administration of drug-containing microcapsules resulted in significantly increased bone mineral contents, demonstrating the excellent osteogenic promoting activity of the pharmaceutical composition of the present invention.

Test Example 7

25 mg of microcapsule No. 1 containing compound A (content ratio 4%) as obtained in Example 1 was locally administered to fibular fracture model rats by the method described in Test Example 6. After 2 and 3 weeks, bone mineral content was determined. For control, bone mineral content was determined in a group receiving a placebo microcapsule (drug-free microcapsule) and a spontaneous healing group. The results are shown in Table 6.

TABLE 6

| Group | Bone Mineral Increment (mg) | |
|---|---|---|
| | 2 Weeks | 3 Weeks |
| Untreated group | 9.1 ± 1.2 | 7.7 ± 1.4 |
| Placebo microcapsule group | 10.2 ± 1.0 | 9.8 ± 1.7 |
| Drug-containing microcapsule group | 15.2 ± 1.4 | 15.1 ± 2.2 |

The drug-containing microcapsule group was found to have a significantly higher bone mineral content, in comparison with the control groups, demonstrating the excellent osteogenic promoting activity of the pharmaceutical composition of the present invention.

Test Example 8

Figure 2:
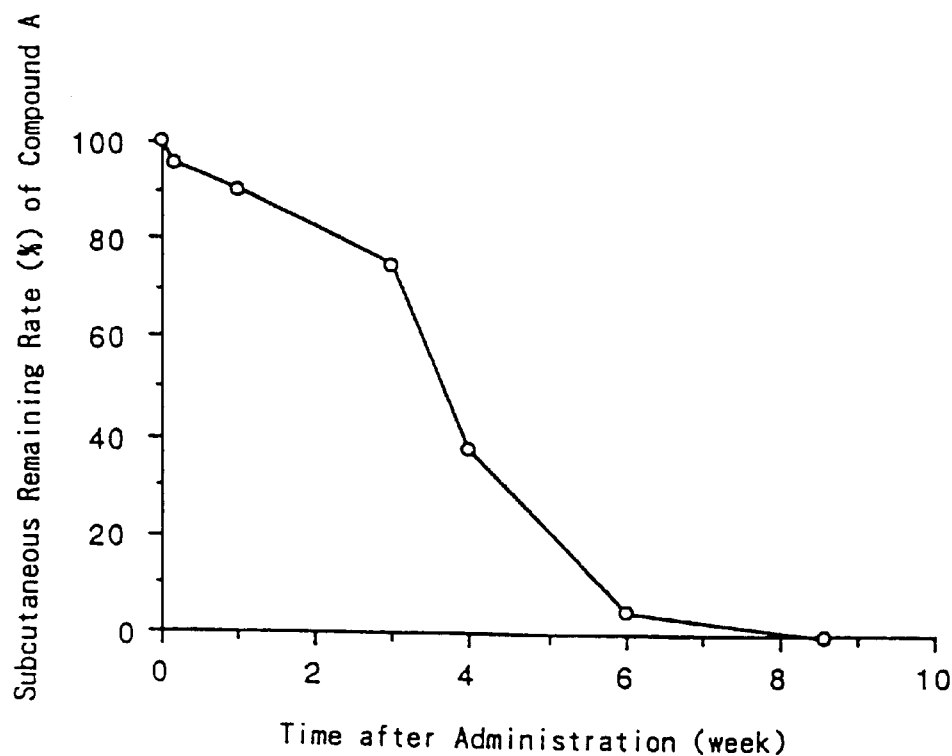
FIG. 2 is a graphic representation of temporal change in compound A retention rate at administration site in rats receiving subcutaneous implantation at their backs of a tablet containing microcapsule containing compound A. The abscissa indicates time (weeks) after administration. The ordinance indicates subcutaneous remaining rate (%) of compound A.

A microcapsule-containing tablet preparation as obtained in Example 5 was subcutaneously implanted in the backs of male SD rats (n=8) at 5 weeks of age under ether anesthesia. The amount of drug remaining at the administration site was determined by HPLC over time. The results are shown in FIG. 2. The subject tablet exhibited a sustained-release property for 6 weeks.

Test Example 9

In accordance with the method of Miyamoto et al. "Shinpei Miyamoto, Hideki Yoshikawa and Kunio Takaoka: The Bone, 7, 85–96 (1983)", tibiae of rabbits (weighing 3 to 4 kg) were cut to form a bone defect 5 mm in length, which was then filled by inserting a microcapsule-containing tablet preparation as obtained in Example 5, and the wound was fixed externally. For control, a placebo microcapsule-containing tablet preparation which does not contain compound A was used. Soft X-ray radiography revealed bone adhesion in rabbits administering the tablet containing compound A 2 months after surgery, while no bone adhesion was noted in the rabbits receiving the placebo tablet.

Test Example 10

Figure 3:
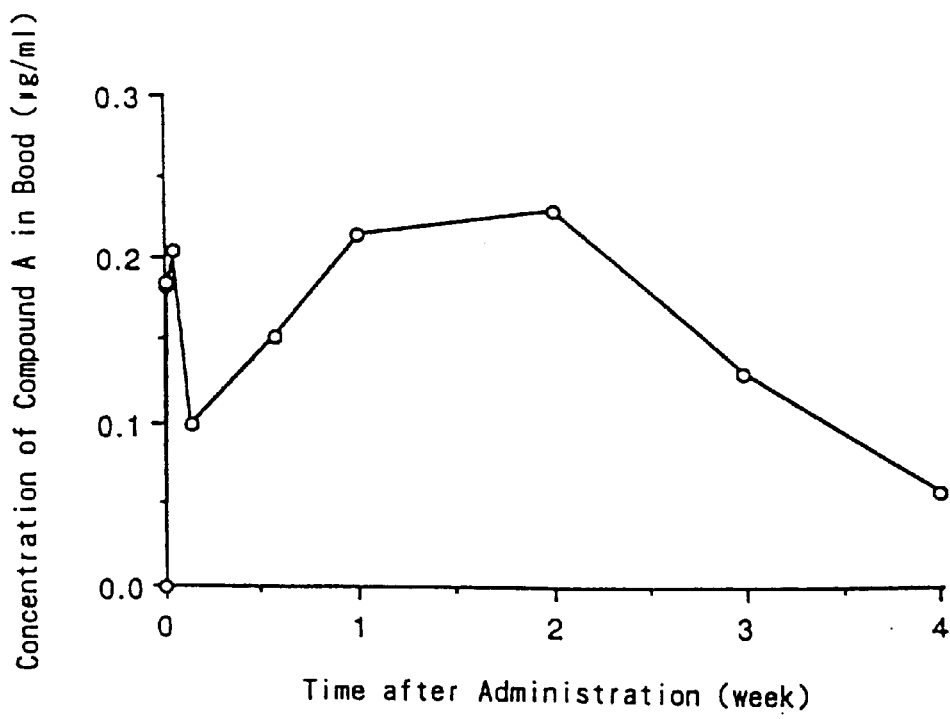
FIG. 3 is a graphic representation of temporal change concentration compound A in blood of rats receiving subcutaneous implantation at their backs of a microcapsule containing compound A. The abscissa indicates time (weeks) after administration. The ordinance indicates concentration (µg/ml) of compound A in blood.

Microcapsule No. 7 containing compound A (content ratio 10%) as obtained in Example 6 was subcutaneously administered to the backs of male SD rats (n=5) at 5 weeks of age under ether anesthesia, by the method described in Test Example 3 (100 mg/kg rat body weight, based on compound A). Blood drug concentration was determined by HPLC over time. The results are shown in FIG. 3. A blood drug concentration of 0.05 to 0.1 $\mu$g/ml was obtained even at 4 weeks after administration.

Test Example 11

A rat fibular fracture model was prepared by the method described in Test Example 6, to which microcapsule No. 7 containing compound A (content ratio 10%) as obtained in Example 6 was locally administered in the form of a lyophilized powder (1 mg/rat) or a suspension in the dispersant described in Test Example 5 (5 mg/0.25 ml/rat). Two weeks later, bone mineral content was determined by the method described in Test Example 6, and compared with the control placebo microcapsule group. The results are shown in Table 7.

TABLE 7

| Group | Bone Mineral Increment (mg) | |
|---|---|---|
| | Lyophilized Powder | Suspension |
| Placebo microcapsule group | 8.3 ± 0.7 | 7.6 ± 0.9 |
| Drug-containing microcapsule group | 12.2 ± 0.8 | 10.2 ± 0.8 |

Whether the drug form was lyophilized powder or suspension, the drug-containing microcapsule group was found to have a significantly higher bone mineral content, in comparison with the control groups, demonstrating the excellent osteogenic promoting activity of the pharmaceutical composition of the present invention.

Test Example 12

A rat fibular fracture model was prepared by the method described in Test Example 6. And microcapsule No. 7 was suspended into a dispersion medium containing various concentration of sodium phosphate which is prepared by adjusting a solution of D-sorbitol (2.5 g), sodium chloride (0.9 g), polysorbate (0.1 g) and carboxymethyl cellulose (0.5 g) in distilled water.

The suspension was locally administered (5 mg/0.25 ml/rat). Two weeks later, bone mineral content was determined by the same method described in Test Example 6. The results are shown in Table 8.

TABLE 8

| Sodium phosphate Content (mM) | Bone Mineral Increment (mg) |
|---|---|
| 0 | 7.0 ± 0.6 |
| 2 | 9.2 ± 1.4 |
| 20 | 9.6 ± 0.5 |
| 100 | 12.0 ± 1.6 |

Effect of the Invention

Showing enhanced osteogenic promoting activity with low toxicity over a long period of time, the pharmaceutical composition of the present invention can be safely used as a prophylactic/therapeutic agent for various bone diseases in mammals, e.g., bone fractures, osteoporosis, osteomalacia, Behcet's syndrome of bone, ankylosing spondylitis, rheumatoid arthritis, gonarthritis deformans, and joint tissue destruction caused by the related diseases, as a bone tissue repairing agent after surgery for multiple myeloma, lung cancer, breast cancer, etc., and as a periodontal tissue regeneration promoter in periodontopathy, etc.

Industrial Applicability

The pharmaceutical composition comprising a non-peptide osteogenic substance and a biodegradable polymer is a useful agent for treating and/or preventing bone diseases.

We claim:

1. A sustained-release pharmaceutical composition comprising a sustained-release microcapsule having a release time of from 1 week to 3 months comprising a composition comprising (2R,4S)-(−)-N-[4-(diethoxyphosphorylmethyl)phenyl]-1,2,4,5-tetrahydro-4-methyl-7,8-methylenedioxy-5-oxo-3-benzothiepine-2-carboxamide and a biodegradable polymer.

2. A pharmaceutical composition according to claim 1, which further comprises a phosphoric acid or its salt.

3. A pharmaceutical composition according to claim 1, which is in a form suitable for local administration.

4. A pharmaceutical composition according to claim 1, which is in a form suitable for promotion of bone fracture healing.

5. A pharmaceutical composition according to claim 1, wherein the ratio by weight of said biodegradable polymer based on said osteogenic promoting pharmaceutical composition is about 1 to 100 times.

6. A pharmaceutical composition according to claim 1, which further comprises a phosphoric acid or its salt.

7. A pharmaceutical composition according to claim 6, wherein the phosphoric acid or its salt is sodium phosphate.

8. A pharmaceutical composition according to claim 1, wherein the content ratio of (2R,4S)-(−)-N-[4-diethoxyphosphorylmethyl)phenyl]-1,2,4,5-tetrahydro-4-methyl-7,8-methylenedioxy-5-oxo-3-benzothiepine-2-carboxamide based on the biodegradable polymer is about 5 to 30% (w/w), and the content ratio of sodium phosphate based on (2R,4S)-(−)-[N-(diethoxyphosphorylmethyl) phenyl]-1,2,4,5-tetrahydro-4-methyl-7,8-methylenedioxy-5-oxo-3-benzothiepine-2-carboxamide and the biodegradable polymer is about 0.1 to 20% (w/w).

9. A pharmaceutical composition according to claim 1, wherein the biodegradable polymer is a lactic acid-glycolic acid copolymer.

10. A pharmaceutical composition according to claim 9, wherein the ratio of lactic aicd/glycolic acid is about 90/10 to 50/50 (w/w) and the weight-average molecular weight is about 8000 to 50000.

11. A pharmaceutical composition according to claim 1, wherein the biodegradable polymer is an aliphatic polyester.

12. A pharmaceutical composition according to claim 11, wherein the aliphatic polyester is a lactic acid-glycolic acid copolymer.

13. A pharmaceutical composition according to claim 1, which is in the form of a suspension.

14. A pharmaceutical composition according to claim 1, which is in a form suitable for injection.

15. Method for treating or preventing bone diseases in mammals which comprises administrating to a subject in need an effective amount of a pharmaceutical composition according to claim 1.

16. Method according to claim 15, wherein the bone diseases are bone fractures.

* * * * *